United States Patent [19]

D'Arrigo

[11] Patent Number: 5,558,866
[45] Date of Patent: Sep. 24, 1996

[54] ANTINEOPLASTIC CHEMOTHERAPEUTIC OF PLANT ORIGIN, HAVING HIGH SELECTIVITY AND GREATLY REDUCED TOXICITY, AND PROCESS FOR THE PREPARATION THEREOF

[76] Inventor: Claudio D'Arrigo, 2 Via Elea, I-00183 Roma RM, Italy

[21] Appl. No.: 961,695

[22] PCT Filed: May 22, 1992

[86] PCT No.: PCT/IT92/00057

§ 371 Date: Jan. 28, 1993

§ 102(e) Date: Jan. 28, 1993

[87] PCT Pub. No.: WO92/21359

PCT Pub. Date: Dec. 10, 1992

[30] Foreign Application Priority Data

May 29, 1991 [IT] Italy .................................. RM91A0372

[51] Int. Cl.$^6$ .................................................. A61K 35/78
[52] U.S. Cl. ........................................ 424/195.1; 514/783
[58] Field of Search ........................................ 424/195.1

[56] References Cited

PUBLICATIONS

Chemical Abstract, vol. 72, 75619d (1970).
"Triterpenoid Sapogenins From Leaves of *Pittosporum undulatum,*" *Phytochemistry*, vol. 22, No. 5, pp. 1235–1237 (1983).
"Triterpenoid Saponins From Leaves of *Pittospurum undulatum*", *Phytochemistry*, vol. 22, No. 11, pp. 2565–2569 (1983).
Chemical Abstract, vol. 94, 1274b (1981).
Saponin and Sapogenol. VI$^{1)}$ Sapogenol Constituents of Leaves of *Pittosporum tobiran* Ait., by I. Yosioka et al, *Chem. Pharm. Bull.*, 20(7), 1499–1506 (1972).
Terpenes From Pittosporaceae, by E. Nemethy et al, *Phytochemistry*, vol. 21, No. 12, pp. 2981–2982 (1982).
"The Structure of a New Sesquiterpene Glycoside from the Flowers of *Pittosporum tobira*", by T. Suga et al, *Chemistry Letters*, pp. 445–448, 1988.
Chemical Abstract, vol. 104, 31777d (1986).
Chemical Abstract, vol. 77, 149711e (1972).
Chemical Abstract, vol. 72, 705v (1970).
Chemical Abstract, vol. 83, 128752c (1975).
Jay, M. et al, *Phytochemistry*, 1974, vol. 13, pp. 1565–1569.
*Index of Garden Plants* Ed. Mark Griffiths, pp. 902–903, (The MacMillan Press Ltd.), 1994.
"Journal of Natural Products" vol. 41, 1978—pp. 463–471. D. A. Van Den Berghe et al Screening of Higher Plants For Biological Activities.
"Screening of High Plants For Biological Activities" vol. 36, 1979 pp. 311–321—Margaretha Ieven et al.

*Primary Examiner*—John Kight
*Assistant Examiner*—Howard C. Lee
*Attorney, Agent, or Firm*—Birch, Stewart, Kolasch & Birch, LLP

[57] ABSTRACT

The invention relates to active principles having an antineoplastic action, extracted from plants of the family Pittosporacee, and to pharmaceutical preparations based on at least one of the substances or compositions to be found in said extracts. With respect to other known antitumoral drugs, these antineoplastic chemotherapeutic drugs show greater selectivity towards degenerated cells and a lower level of interference with the metabolism of healthy cells. The invention also extends to the process for extraction and separation of the components of the extracts and to their use for the preparation of antineoplastic drugs or drugs for the treatment of other pathologies.

25 Claims, No Drawings

ID OF PLANT ORIGIN, HAVING HIGH
SELECTIVITY AND GREATLY REDUCED
TOXICITY, AND PROCESS FOR THE
PREPARATION THEREOF

DESCRIPTION

The present invention has as its subject substances and compositions having an antineoplastic activity, extracted from plants of the family Pittosporaceae, pharmaceutical preparations based on at least one of said substances and compositions, and processes for the extraction and, respectively, formulation thereof.

As it is known, one of the most promising lines of research which, at least from a theoretical point of view, is of easy application in research aimed at eliminating neoplastic diseases, is that of antitumoral chemotherapy. The antiproliferating agents which have been isolated up to the present time are of widely differing origins and heterogeneous chemical characteristics. Among these antiproliferating agents are also certain substances extracted from plants such as colchicine and vincaleucoblastin, the former extracted from *Colchicum Autumnale* and the latter from *Vinca Rosea*. Although these antiproliferating substances are more or less provided with a certain specifically antitumoral activity, their selectivity towards degenerated cells is generally rather poor. The danger deriving from the possibility of their interfering with the metabolism of healthy cells thus forms an important obstacle to their wider use.

It has now been surprisingly found that the present invention makes it possible to overcome the above mentioned limitations, providing a chemotherapeutic antineoplastic agent based on active principles of plant origin and provided with highly selective antitumoral activity and a toxicity level much lower than that of other antitumoral drugs.

First of all, the subject matter of the present invention is a process for obtaining substances and/or compositions having an antineoplastic activity, characterized by the fact that parts and/or products of plants from the family Pittosporacea—in whatever stage of their development or maturity—are made to undergo essentially the following operations:

a) extraction of components by maceration in an organic solvent:
b) optional stirring or shaking of the solution containing the extract with another solvent, at least partially miscible with the first, to distribute the components of the extract among the phases formed;
c) optional treatment of each phase, independently from each other, with at least one further organic liquid having the properties of solvent for at least one of the components in the extract, followed by filtering of any suspension which may have formed and collection of the solid phase and its successive purification;
d) optional separation of the components found in each liquid phase; and
e) collection of the separated components with antineoplastic activity and those without antineoplastic activity.

The extracts can be dried and purified before each further stage of the process.

The plants of the family Pittosporacea are preferably of the genus Pittosporum. In this sense, the plants can be selected, for example, from the group comprising *Pittosporum ondulatum, Pittosporum coriaceum, Pittosporum viridicolor, Pittosporum rhombipholium, Pittosporum eugenoides, Pittosporum crossifolium* and *Pittosporum Tobira* and combinations thereof.

The solvent can be an alcohol. Good results have been obtained using ethyl alcohol.

The volume ratio between organic solvent and plant parts to be treated is preferably comprised between 1:10 and 10:1.

The treatment times are preferably comprised between 5 minutes and 3 months. The treatment temperatures can vary preferably between 5° C. and 100° C.

Separation of the components from the extract can be preferably of the chromatographic type. Good results have been obtained using chromatography on a silica gel column or on an HPLC preparatory column.

Extraction can be performed using ethanol and collecting the components which have HPLC retention times of about 1,157, 1.545, 1,883, 2,051, 2.273, 2,572 and 2,743.

(It must be specified that the analytic tests in HPLC, both in this case and in the following ones, were carried out using a Perkin-Elmer series 250 chromatograph with a 125 mm·4 mm RP 18 column with a mobile phase consisting of methanol-$H_2O$ (80:20) and a wave length equal to 210 nm).

After extraction with ethanol, the solution thus obtained can be shaken with chloroform forming two phases, an alcohol-chloroform phase of an intense green color and an aqueous phase of an orange-yellow color. In this case the components having an antineoplastic activity are found in the alcohol-chloroform phase. Collection of the components having antineoplastic activity is performed chromatographically after having dried out the alcohol-chloroform phase and having resolubilized the solute in methanol. Performing chromatography on the methanolic solution using the HPLC technique, the components having retention times of about 1.969, 2.296 and 2.756 are collected.

The alcohol-chloroform solution can be concentrated by evaporation and isopropyl alcohol can be added to form a suspension that is filtered, the solid phase having been heat dried and powdered in a mortar. After being resolubilized in ethanol-water it can then be purified on a chromatographic column of active carbon. The two solid fractions (impure and pure) dissolved in ethanol-water or in methanol can be chromatographed using the HPLC technique, collecting the components with retention times of about 1.157, 1.545 and 2.264.

The invention also refers to substances and compositions per se, characterized by the fact that they are obtainable using the process described above.

The subject matter of the present invention are also substances and compositions having an antineoplastic activity, characterised by the fact that they are obtainable using the process mentioned above.

The substances and compositions having an antineoplastic activity can be treated to form salts, compounds or complexes, in order to make them water soluble.

The present invention further comprises a pharmacutical preparation, characterized by the fact that it contains as at least one of its active principles a substance or composition selected from the group of substances or compositions having an antineoplastic activity which are obtainable from the process described above, or combinations thereof.

The pharmaceutical preparation can be selected from the group comprising aqueous solution for parenteral use, capsules for oral use, suppositories for rectal use, ovules for use in the vagina, unguents, salves, cremes and gels.

The aqueous solution can be in vials. Each vial contains between 0.1 and 2.5 g of active principle, preferably between 0.1 and 1.5 g, more preferably between 0.2 and 1.0 g of active principle.

In the case of a pharmaceutical preparation in the form of a capsule, each capsule contains 0.2–2.0 g of active principle, preferably 0.8–1.2 g of active principle.

In the case of a pharmaceutical preparation in the form of a suppository for rectal use, each suppository contains between 0.2 and 2.5 g of active principle, preferably between 0.3 and 1.0 g or between 1.2 and 1.7 g of active principle.

In the case of a pharmaceutical preparation in the form of an ovule for use in the vagina, each ovule contains between 0.1 and 2.5 g of active principle, preferably between 0.5 and 2.5 g, more preferably between 0.3 and 1.7 g of active principle.

In the case of a pharmaceutical preparation in the form of an unguent, a salve, a creme or a gel, the local excipient contains between 0.5 and 12% of active principle, preferably between 3 and 7% of active principle.

The invention further refers to the use of the components obtainable using the extraction, separation and collection process given above, either alone or in combination, for the preparation of drugs for the treatment of various pathologies other than neoplastic ones.

Up to now the objects of the present invention have been described in a general manner. With the aid of the following examples, a more detailed description will now be given to clarify the extent, characteristics, advantages and operating methods of the invention.

EXAMPLE 1

Method for the extraction and purification of the active principles 1 kg of unripe fruits of the Pittosporum Tobira were finely ground and infused at room temperature with a quantity of ethyl alcohol at 95° sufficient to cover the ground fruits (approximately 1:1 by volume). The mixture is left to steep for at least 30 days, then filtered. The 1000 ml of alcoholic extract, obtained as described above, are put into a separating funnel together with the same volume of chloroform. After stirring a number of times, separation occurs, which is completed after 24 hours of mixing: in the lower part of the funnel an alcohol-chloroform solution of an intense green color is separated off; in the upper part of the funnel an aqueous solution of a yellow-orange color (orange soluble fraction=OSF), formed by the hydrosoluble substances extracted from the water initially present in the fruit. OSF is present in an amount of approximately 20% by volume and is formed almost exclusively of components which have an RT in HPLC of 1.141 (3.45% area), 1.440 (24.46% area) and 1.593 (61.93% area). The OSF substance, equal to approximately 73% by weight of the dry substance of the total alcoholic extract, is formed by a yellowy-white powder which not only is completely inactive on experimental tumors, but actually aids their evolution, causing it to become more rapid. This substance is therefore removed. The residual alcohol-chloroform solution is evaporated at 30° C. in a rotavapor and dried out. An amorphous substance is obtained, dark green in color, which, once it has been resolubilized in methanol (1 mg/ml) and analyzed using HPLC, shows a notable concentration of active peaks with retention times ranging from 1.969 (7.83% area) to 2.296 (40.12% area) to 2.756 (1.47% area).

EXAMPLE 2

Method for purification of the active principles

The alcohol-chloroform solution left over from the operations performed in example 1 (made up of total alcoholic extract less OSF), is evaporated in a flask in a rotavapor at 45° C. until concentrated to a volume of approximately 30 ml (approximately 1/35 of the total starting alcoholic extract). At this point, a quantity of isopropylic alcohol equal to 30% of the total initial alcoholic extract (300 ml) is added to the flask. A suspension is formed, as a part of the substances obtained in the total alcoholic extract less OSF, which was soluble both in ethanol and in methanol, is no longer soluble in isopropanol.

The suspension thus obtained is set to filter on rapid filter paper. The precipitate which is deposited on the paper is heat dried at a temperature of 45° C. Once dry, it is finely ground in a porcelain mortar. Approximately 1500 mg of a yellow-greenish powder are thus obtained. This powder (which hereinafter will be referred to as CIDI), solubilized in methanol and examined using the usual HPLC method, shows RTs of 1.157 (78.83% area), 1.545 (16.25% area) and 2.264 (4.91% area).

Alternatively, using a Supelcosil LC—$NH_2$-5µ-spherical column, mobile phase $CH_3CN$—$H_2O$ (3:1) for a flow rate of 1.5 ml/m and an UV detector at 217 nm, the following RT values were obtained: 1.889 (concentration 53.88); 2.640 (20.89); 3.145 (4.61); 3.420 (5.08); 3.942 (6.16); 4.722 (4.53); 5.255 (3.253); 6.287 (0.90) and 6.982 (0.66).

On a Chromopack-Lichrosorb RP 18-10 µ-irregular column, with the same eluent, flow and marker, the following peaks were obtained: 1.460 (concentration 65.98); 1.965 (20.87); 2.535 (1.86); 2.704 (2.05); 3.097 (1.74); 3.395 (3.38); 4.324 (0.85); 4.609 (0.93); 9.597 (0.88); 10.017 (1.42).

The substance CIDI presents a 3.17% residue on calcination. The elementary analysis in % by weight (without taking the residue into account) is the following: C 54.25%; H 7.58% ; O 38.17% with a minimal empirical formula close to $C_{15}H_{25}O_8$ and m.p. (dec.) 196°–222° C. The IR spectrum (IR spectrophotometer Perkin-Elmer Mod. 683) in KBr medium, concentration 1 mg/100 mg, shows the following observable bands:

3400 $cm^{-1}$ stretching OH associated; 2960 $cm^{-1}$ asymmetrical stretching $CH_3$; 2920 $cm^{-1}$ asymmetrical stretching $CH_2$; 1720 $cm^{-1}$ stretching C=O; 1610 $cm^{-1}$ asymmetrical stretching C=O of $COO^-$; 1460 $cm^{-1}$ bending $CH_3$; 1380 $cm^{-1}$ bending $CH_3$ (typical of $OCOCH_3$); 1250 $cm^{-1}$ bending OH; 1150, 1080 and 1040 $cm^{-1}$ stretching C—O.

UV spectrum (spectrophotometer UV-vis Perkin-Elmer mod. Lambda 5):

1) Solution in $CH_3OH$—$H_2O$ (4:1), concentration $6\times10^{-2}$ mg/ml:

maximum absorption at 202 nm; absorption quickly decreases up to 260 nm, remains constant in the range 260–330 nm, and then decreases again;

2) Solution in $CH_3CN$—$H_2O$ (3:1), concentration $6\times10^{-2}$ mg/ml:

absorption quickly decreases from 200 to 260 nm, remains almost constant in the range 260–330 nm, and then decreases again.

CIDI powder is insoluble in acetone, benzene, chloroform, ethyl ether, petroleum ether, ethyl alcohol, isopropyl alcohol; it is soluble in methanol and water.

The aqueous solution of CIDI has a pH of 6.5.

The $LD_{50}$ on mice Crl: CD-1 (ICR) BR is 1274.9 mg/kg (fiducial limits 1041.2–1561.0 mg/kg) orally and 25 mg/kg (fiducial limits 23.0–27.2 mg/kg) intraperitoneally.

EXAMPLE 3

Further method of purification of the active principles 10 g of CIDI powder, obtained according to the process of examples 1 and 2, were solubilized in 1000 ml of a solution of ethyl alcohol and water (4:1), obtaining a solution at 1% of a green color. A chromatograph column with a diameter of 4.5 cm was prepared, provided with a porous separator. On the separator is laid a layer of cotton wool, then a layer of sand approximately 3 cm high. A suspension containing 35 g of active carbon in ethanol is then poured on. Once the active carbon has packed tightly, the solution of CIDI powder (solubilized as described above) is made to pass through the chromatographic column. Once all the CIDI solution has passed through the chromatographic column, the column is washed by passing 1000 ml of the solvent alone (ethyl alcohol—$H_2O$ 4:1)

A limpid, colorless solution is obtained, which is concentrated to its maximum limit in a rotavapor at a temperature of 45° C.

Crystallization takes place after addition of isopropyl alcohol. Once dried, again in a rotavapor, and ground in a mortar, a white powder is obtained, which will hereinafter be indicated as pure CIDI. Pure CIDI corresponds to 60% CIDI by weight.

The pure CIDI powder, solubilized in methanol and examined using the usual HPLC method, shows two main peaks with RT values of 1.131 (87.54% area) and 1.551 (6.16% area).

On the contrary, HPLC with UV detector at 217 nm, movable phase $CH_3CN$—$H_2O$ (3:1), flow rate 1.5 ml/m gives the following RT (main peaks):
1) on Supercosil LC-$NH_2$-5μ-spherical column: 1.885 (conc. 19.60); 16.259 (conc. 67.51);
2) on Chrompack-Lichrosorb RP18-10μ-irregular column: 1.617 (conc. 87.74); 1.985 (3.69) and 2.134 (2.20).

Pure CIDI is a white water-soluble solid which has a calcination residue of 3.05%.

The elementary analysis in % by weight (without taking into account the residue) is: C 48.82% H 7.06%; O 44.12% with a minimal empirical formula close to $C_6H_{10}O_4$ and m.p. (dec.) 205°–255° C.

The IR spectrum is practically the same as that of the product CIDI.

UV spectrum (spectrophotometer UV-vis Perkin Elmer mod. Lambda 5):
1) solution in $CH_3OH$—$H_2O$ (4:1), concentration $6\times10^{-2}$ mg/ml:
maximum absorption at 203 nm; absorption quickly decreases, practically no absorption is observed above 260 nm;
2) solution in $CH_3CN$—$H_2O$ (3:1), concentration $6\times10^{-2}$ mg/ml:
absorption quickly decreases from 200 to 260 nm, then remains constant at a level close to zero.

The solubility of pure CIDI is the same as that of CIDI, and also the pH of the aqueous solution is the same.

The intraperitoneal $LD_{50}$ of pure CIDI on mice Crl: CD-1 (ICR) BR is 20.2 mg/kg (fiducial limits 17.8–22.0 mg/kg).

NMR spectra of CIDI and pure CIDI:

The NMR spectra have been carried out with an apparatus Bruker AC 200 at 200 $MH_z$ (proton) and 50 $MH_z$ (carbon). The samples have been prepared by dissolving 90 mg of product into 0.6 ml of DMSO-d6 with the addition of 10 mg of the sodium salt of 3 -(trimethylsilyl) propanesulphonic acid (DSS) as internal standard.

For $^1H$ spectra 1000 transients have been accumulated by using an impulse of 30°; the FID have been subjected to a Gaussian multiplication in order to increase the resolution. The exchange of mobile protons has been carried out by adding $D_2O+CF_3COOH$.

For $^{13}C$ spectra 6200 transients (CIDI) and 14900 transients (pure CIDI) have been accumulated by using an impulse at 90° with eteronuclear de-coupling in CPD.

From the examination of $^1H$ spectra derives the presence of several mobile protons in the range 3–5 ppm. The presence of a number of protons of alkylic type is noted, the alkylic protons decreasing at lower ranges. Possible presence of some vinyl proton; and absence of aromatic protons. The $^{13}C$ spectra confirm the above data, with the presence of a great number of alkylic carbons more or less substituted. The presence of some peaks in the vinyl range and of some peaks in the carbonyl range are noted, the carbonyl groups being of acidic or esteric type.

The spectra examination evidentiates no substantial differences between the two mixtures. A difference in the percentage of the various components would appear to be possible.

EXAMPLE 4

Method for chromatographic separation of the active principles

The alcohol-chloroform solution, obtained according to example 1, is dried out in a rotovapor and resolubilized in a small amount of methanol (100 ml). Using this solution, chromatographic separation is carried out both on a silica-gel column and, with greater care, on an HPLC preparative column. Pure fractions are thus obtained which, as stated above, correspond to the peaks 1.157; 1.545; 1.883; 2.051; 2.273; 2.572 and 2.743.

EXAMPLE 5

Tests to underline the antineoplastic activity both in vitro and in vivo

The substances and/or compositions obtained according to the preceding examples, either soluble or solubilized using surface-active agents (Polisorbato 80 or Geronol) in water, show marked antineoplastic activity, together with acceptable toxicity levels and an absence of immunosuppressant activity. The notable selective antineoplastic activity on tumoral cells has been demonstrated, at a histological level, both in vitro and in vivo, by evident alterations in the tumoral cells, which appear to increase in volume, conglutinate, show extroversion and fraying of the cell membrane, an extremely vacuolated and frothy cytoplasm with hypochromia of the nuclear chromatin and pallid nucleoles. Proof of the high selectivity possessed by these substances is given by the fact that all the lesions listed above are totally absent from the normal cells made to undergo the same treatment.

In vivo, the antineoplastic activity of the substances mentioned above was tested on Sa 180 of Swiss mouse, generally using a dose ranging from 2 to 25 mg/Kg/day, according to the substance used, given intraperitoneally for 8 consecutive days, starting from the day following that of the transplant. In comparison with an average survival rate of 25.8 days in the control animals, rejection of the tumor was seen in 90% of the treated animals, which are to be considered as definite survivors.

For therapeutic application, the substances according to the present invention, and their salts, compounds or complexes, are preferably used in the form of aqueous solution for intramuscular, endovenous or endocavitary injection.

I claim:

1. A process for producing an antineoplastic substance, comprising:

(a) macerating an unripened fruit of a plant of the family Pittosporaceae in an alcohol to produce an alcoholic extract;

(b) stirring or shaking said alcoholic extract of step (a) with chloroform to produce an alcohol-chloroform phase and an aqueous phase;

(c) concentrating said alcohol-chloroform phase of step (b) by evaporation to produce a concentrated alcohol-chloroform phase;

(d) adding isopropyl alcohol to said concentrated alcohol-chloroform phase of step (c) to form an isopropyl alcohol suspension;

(e) filtering said isopropyl alcohol suspension of step (d) to produce a precipitate;

(f) drying and grinding said precipitate of step (e) to produce a powder;

(g) solubilizing said powder of step (f) in ethyl alcohol:water, 4:1, to produce a solution;

(h) purifying said solution of step (g) using active carbon, followed by washing said active carbon with ethyl alcohol:water, 4:1, to obtain a limpid, colorless solution;

(i) concentrating said limpid, colorless solution of step (h) to produce a concentrated solution;

(j) adding isopropyl alcohol to said concentrated solution of step (i) to product an isopropyl alcohol suspension; and (k) drying said isopropyl alcohol suspension of step (j) and grinding the dried product to produce a powder.

2. The process according to claim 1, wherein said plant is a member of the genus Pittosporum.

3. The process according to claim 2, in which said plant is selected from the group consisting of *Pittosporum ondulatum, Pittosporum coriaceum, Pittosporum viridicolor, Pittosporum rhombipholium, Pittosporum eugenoides, Pittosporum crossifolium, Pittosporum tobira,* and combinations thereof.

4. The process according to claim 1, wherein the ratio by volume of said alcohol to said unripened fruit is between 1:10 and 10:1.

5. The process according to claim 1, wherein the treatment times are between 5 minutes and 3 months.

6. The process according to claim 1, wherein the treatment temperature is between 5° C. and 100° C.

7. The process according to claim 1, wherein maceration is performed using ethanol and the alcoholic extract obtained is shaken with chloroform to form an alcohol-chloroform phase of an intense green color and an aqueous phase of a yellow-orange color, wherein said antineoplastic substance is present in the intense green phase.

8. The process according to claim 7, wherein the alcohol-chloroform phase is evaporated until reduced to approximately 1/35 by volume of the volume of the alcoholic extract.

9. An antineoplastic substance produced by the process of claim 1.

10. A pharmaceutical preparation, comprising an antineoplastic substance produced by the process of claim 1.

11. The pharmaceutical preparation according to claim 10, prepared in the form of an aqueous solution for parenteral use.

12. The pharmaceutical preparation according to claim 10, prepared in the form of capsules for oral use.

13. The pharmaceutical preparation according to claim 22, prepared in the form of suppositories for rectal use.

14. The pharmaceutical preparation according to claim 10, prepared in the form of ovules for use in the vagina.

15. The pharmaceutical preparation according to claim 10, prepared in the form of an unguent, salve, cream or gel.

16. The pharmaceutical preparation according to claim 11, prepared in vials, each vial containing between 0.1 and 2.5 g of said antineoplastic substance.

17. The pharmaceutical preparation according to claim 16, in which each vial contains between 0.1 and 1.5 g of said antineoplastic substance.

18. The pharmaceutical preparation according to claim 12, prepared in the form of capsules, each capsule containing between 0.1 and 2.0 g of said antineoplastic substance.

19. The pharmaceutical preparation according to claim 18, in which each capsule contains from 0.8 to 1.2 g of said antineoplastic substance.

20. The pharmaceutical preparation according to claim 13, prepared in the form of suppositories for rectal use, each suppository containing between 0.2 and 2.5 g of said antineoplastic substance.

21. The pharmaceutical preparation according to claim 20, in which each suppository contains between 0.3 and 1.0 g of said antineoplastic substance.

22. The pharmaceutical preparation according to claim 14, prepared in the form of ovules for use in the vagina, each ovule containing between 0.1 and 2.5 g of said antineoplastic substance.

23. The pharmaceutical preparation according to claim 22, in which each ovule contains between 0.5 and 2.5 g of said antineoplastic substance.

24. The pharmaceutical preparation according to claim 15, prepared in the form of an unguent, salve, cream or gel, with an excipient for topical use, containing between 0.5 and 12% of said antineoplastic substance.

25. The pharmaceutical preparation according to claim 24, in which said excipient for topical use contains between 3 and 7% by weight of said antineoplastic substance.

* * * * *